United States Patent [19]

Kroenke

[11] 4,225,484

[45] Sep. 30, 1980

[54] TRIPENTYLAMMONIUM DECAMOLYBDATE AND COMPOSITION CONTAINING SAME

[75] Inventor: William J. Kroenke, Brecksville, Ohio

[73] Assignee: The B. F. Goodrich Company, Akron, Ohio

[21] Appl. No.: 49,253

[22] Filed: Jun. 18, 1979

[51] Int. Cl.$^3$ .............................................. C07F 11/00
[52] U.S. Cl. ........................... 260/45.75 R; 260/429 R
[58] Field of Search ..................... 260/429 R, 45.75 R

[56] References Cited

U.S. PATENT DOCUMENTS

| | | |
|---|---|---|
| 2,909,541 | 10/1959 | Hugel ............................... 260/429 R |
| 2,938,869 | 5/1960 | Hugel ........................... 260/429 R X |
| 3,223,625 | 12/1965 | Cyphers ....................... 260/429 R X |
| 3,282,838 | 11/1966 | Knowles et al. ...................... 252/49.7 |
| 3,290,245 | 12/1966 | Elliott et al. ......................... 252/32.7 |
| 3,349,108 | 10/1967 | Marzluff ........................... 260/429 R |
| 3,489,775 | 1/1970 | de Roch et al. ................... 260/348.5 |
| 4,053,455 | 10/1977 | Kroenke ....................... 260/45.75 R |
| 4,153,792 | 5/1979 | Kroenke ............................ 260/429 R |
| 4,164,473 | 8/1979 | Coupland et al. ............... 260/429 R |

*Primary Examiner*—Helen M. S. Sneed
*Attorney, Agent, or Firm*—James R. Lindsay

[57] ABSTRACT

Tripentylammonium decamolybdate is described as a novel amine molybdate and as a smoke retardant additive for vinyl chloride and vinylidene chloride polymer compositions.

4 Claims, No Drawings

TRIPENTYLAMMONIUM DECAMOLYBDATE AND COMPOSITION CONTAINING SAME

BACKGROUND OF THE INVENTION

Amine molybdates may be produced by reacting an amine with a molybdenum compound such as molybdenum trioxide ($MoO_3$), molybdic acid or a molybdenum salt in an acidic aqueous medium made acidic through the addition of a suitable acid such as an organic acid containing 1 to 12 carbon atoms (exemplified by acetic acid, propionic acid, benzoic acid, and the like) or an inorganic acid (exemplified by hydrochloric acid, nitric acid or sulfuric acid. The acidic mixture is refluxed, preferably while being stirred continuously, until the reaction is complete, usually for about ¼ to 4 hours.

Amine molybdates also may be produced, as described in my co-pending application Ser. No. 016,583, filed Mar. 1, 1979 and entitled "Process For Making Amine Molybdates", by reacting essentially stoichiometric quantities of molybdenum trioxide with an amine in an aqueous medium essentially free of acid and in which a water-soluble ammonium or monovalent metal or divalent metal or trivalent rare earth metal salt of an inorganic or organic acid is dissolved.

The particular amine molybdate formed may depend upon which process is used to form the amine molybdate and the quantity of reactants present in the reaction mixture, as well as the reaction conditions.

SUMMARY OF THE INVENTION

The present invention pertains to a novel amine molybdate, namely, tripentylammonium decamolybdate, which may be represented by the empirical formula $[H.(C_5H_{11})_3N]_4Mo_{10}O_{32}$ $N(H_2O)$, where "n" can be an integer of from 0 to 4, and which exhibits major x-ray diffraction peaks at "d" spacings of 12.1Å, 11.6Å, 8,62Å and 8.34Å. Like many other amine molybdates, tripentylammonium decamolybdate functions as an effective smoke retardant additive for vinyl chloride and vinylidene chloride polymers.

DETAILED DESCRIPTION OF THE INVENTION

Tripentylammonium decamolybdate may be produced by reacting ammonium dimolybdate [$(NH_4)_2Mo_2O_7$] and tripentylamine is essentially a 2/1 molybdenum/tripentylamine molar ratio in an acidic aqueous medium. Suitable acids include inorganic acids such as hydrochloric acid, nitric acid, sulfuric acid and the like, or mixtures thereof. The amount of acid used may be varied widely from about ½ to 10 or more molar equivalents of acid per molar equivalent of ammonium dimolybdate. However, about a 1/1molar equivalent ratio is preferred. Sufficient water is included in the reaction mixture to insure a reaction medium that has a consistency that enables it to be easily stirred. Desirably, the ammonium dimolybdate is dissolved in water and is added to an acidic solution of the tripentylamine. If preferred, the ammonium dimolybdate, tripentylamine, acid and water can be charged essentially simultaneously to the reaction vessel. The reaction materials desirably are refluxed while being stirred continuously for 0.25 to 16 hours. Although the reaction can occur at room temperature (25° C.), desirably the reaction mixture is heated to between 75° to 110° C. in order to reduce the time for the reaction to be completed. After the reaction is completed, the solid crystalline tripentylammonium decamolybdate formed can be separated from the liquid phase by filtration, centrifugation or other suitable separation means, washed with water, alcohol or a mixture of water and alcohol, and then dried. The reaction mixture may be cooled to about room temperature (about 25° C.) before the separation of the tripentylammonium decamolybdate from the liquid phase, although cooling the mixture before separation of the solid product from the liquid phase is not necessary. The recovered tripentylammonium decamolybdate may be air dried, preferably at about 100° to 200° C., or may be vacuum dried, preferably at temperatures up to 150° C. and higher. The tripentylammonium decamolybdate is readily identifiable by elemental, infrared or x-ray diffraction analysis.

Alternatively, the tripentylammonium decamolybdate can be prepared by reacting together essentially stoichiometric quantities of molybdenum trioxide with tripentylamine in an aqueous medium essentially free of acid and in which a water-soluble ammonium or monovalent metal or divalent metal or trivalent rare earth metal salt of an inorganic or organic acid is dissolved. Sufficient water is included in the reaction mixture to insure a reaction medium that has a consistency that enables it to be easily stirred. The water-soluble ammonium or monovalent metal or divalent metal or trivalent rare earth metal salt may be a salt of a strong acid (HCl, $HNO_3$ and $H_2SO_4$) or of a weak acid (such as carbonic acid, acetic acid, formic acid, benzoic acid, salicyclic acid, oxalic acid, sebacic acid and adipic acid). A combination of one or more of the water-soluble salts can be used. The water-soluble salt desirably is present in the reaction mixture in an amount to form at least a 1:1 mole ratio with the molybdenum trioxide. The reaction time for obtaining the highest yield of tripentylammonium decamolybdate will vary depending in part upon the temperature at which the reaction is occurring and the amount of excess water-soluble salt present in the reaction mixture. The reaction usually is completed within 4 hours and, when the water-soluble salt is present in about a 50 percent excess, may be completed in ¼ to 2 hours or even less. The reaction mixture usually is stirred continuously while being refluxed during the time the reaction is occurring. Desirably, the reaction mixture is heated to between 75° to 110° C. during the reaction, although the reaction can take place at room temperature (25° C.). After the reaction is completed, the crystalline tripentylammonium decamolybdate can be separated from the liquid phase, washed and dried in the manner described above.

The following examples illustrate the preparation of tripentylammonium decamolybdate more fully:

EXAMPLE 1

10.00 grams of tripentylamine, 8.67 grams of a 37 percent hydrochloric acid solution and 200 milliliters of water were added to a 1000 milliliter round-bottom flask equipped with a water-cooled condenser and was brought to reflux. 14.95 Grams of ammonium dimolybdate were added to 50 milliliters of water and were heated until dissolved. The hot ammonium molybdate solution was added to the flask and the reaction mixture was refluxed while being stirred continuously for ½ hour. The contents of the flask were cooled to room temperature (about 25° C.) and were filtered. A crystalline solid was recovered. The recovered solid was washed with water and vacuum dried at 100° C. for approximately 4½ hours. 19.80 Grams of the crystalline material were recovered. Elemental and infrared analyses indentified the solid to the tripentylammonium decamolybdate.

EXAMPLE 2

10.00 Grams of tripentylamine, 12.66 grams of molybdenum trioxide, 8.72 grams of ammonium sulfate and 300 milliliters of water were added to a 500 milliliter round-bottom flask equipped with a water-cooled condenser. The mixture was refluxed for 2 hours while being stirred continuously, was cooled to room temperature (about 25° C.) and filtered. A crystalline solid was recovered. The recovered solid was washed with water and was vacuum dried for 5 hours at 100° C. The product was identified by elemental and infrared analyses to be tripentylammonium decamolybdate. 17.48 Grams of the crystalline product were recovered.

Tripentylammonium decamolybdate has been found to be a smoke retardant additive for vinyl chloride and vinylidene chloride polymer compositions. When used as a smoke retardant additive, the tripentylammonium decamolybdate desirably has an average particle size from about 0.01 to about 800 microns, preferably from about 0.1 to about 100 microns, and is present in an amount from about 0.1 to about 20 parts by weight per 100 parts by weight of the vinyl chloride of vinylidene chloride polymers.

Vinyl chloride and vinylidene chloride polymers with which the tripentylammonium decamolybdate can be used as a smoke retardant additive include homopolymers, copolymers and blends of homopolymers and/or copolymers. The vinyl chloride and vinylidene chloride polymers may contain from 0 to about 50 percent by weight of at least one other olefinically unsaturated monomer. Suitable monomers include 1-olefins containing from 2 to 12 carbon atoms such as ethylene, propylene, 1-butene, isobutylene, 1-hexene, 4-methyl-1-pentene and the like; dienes containing from 4 to 10 carbon atoms, including conjugated dienes such as butadiene, isoprene, piperylene, and the like; ethylidene norbornene and dicyclopentadiene; vinyl esters and allyl esters such as vinyl acetate, vinyl chloroacetate, vinyl propionate; vinyl laurate, alkyl acetate, and the like; vinyl aromatics such as styrene, α-methyl styrene, chlorostyrene, vinyl toluene, vinyl naphthalene, and the like; vinyl and allyl ethers and ketones such as vinyl methyl ether, allyl methyl ether, vinyl isobutyl ether, vinyl n-butyl ether, vinyl chloroethyl ether, methylvinyl ketone, and the like; vinyl nitriles such as acrylonitrile, methacrylonitrile, and the like; cyanoalkyl acrylates such as α-cyanomethyl acrylate, the a-, β- and γ-cyanopropyl acrylates, and the like, olefinically unsaturated carboxylic acids and esters thereof, including α,β-olefincally unsaturated acids and esters thereof such as methyl acrylate, ethyl acrylate, chloropropyl acrylate, butyl acrylate, hexyl acrylate, 2-ethylhexyl acrylate, dodecyl acrylate, octadecyl acrylate, cyclohexyl acrylate, phenyl acrylate, glycidyl acrylate, methoxyethyl acrylate, ethoxyethyl acrylate, hexylthioethyl acrylate, methyl methacrylate, ethyl methacrylate, butyl methacrylate, glycidyl methacrylate, and the like; and including esters of maleic and fumaric acid, and the like; amides of the α,β-olefinically unsaturated carboxylic acids such as acrylamide, and the like, divinyls, diacrylates and other polyfunctional monomers such as divinyl benzene, divinyl ether, diethylene glycol diacrylate, ethylene glycol dimethacrylate, methylenebis-acrylamide, allyl pentaerythritol, and the like; and bis (β-chloroethyl) vinyl phosphonate, and the like.

The vinyl chloride and vinylidene chloride polymers, in addition to the tripentylammonium decamolybdate additive, may contain the usual compounding ingredients known to the art such as fillers, stabilizers, opacifiers, lubricants, processing aids, impact modifiers, plasticizers antioxidants, and the like.

Smoke retardancy may be measured using an NBS Smoke Chamber according to procedures described in ASTM E662-79 "Test For Specific Optical Density Of Smoke Generated By Solid Materials". Maximum smoke density ($D_m$) is a dimensionless number and has the advantage of representing a smoke density independent of chamber volume, specimen size or photometer path length, provided a consistent dimensional system is used. Percent smoke reduction is calculated using the equation:

$$\frac{Dm/g \text{ of control} - Dm/g \text{ of sample}}{Dm/g \text{ of control}} \times 100$$

The term "Dm/g" means maximum smoke density per gram of sample. Dm and other aspects of the physical optics of light transmission through smoke are discussed fully in the ASTM publication.

The smoke retardant property of tripentylammonium decamolybdate is illustrated by the following examples.

EXAMPLES 3–5

| Material | Parts by Weight |
|---|---|
| Polyvinyl Chloride Resin* | 100.0 |
| Lubricant** | 2.0 |
| Tin Stabilizer*** | 2.0 |
| Tripentylammonium decamolybdate | varied |

*Homopolymer of vinyl chloride having an inherent viscosity of about 0.98 1.04; ASTM Classification GP-5-15443.
**A commercial polyethylene powder lubricant (Microthene 510).
***Tin thioglycolate The ingredients of the recipe were dry-mixed and banded on a two-roll mill for about 5 minutes at a roll temperature of about 160° C. The milled compositions were pressed into 6×6×0.025 inch sheets. Pressing was done at about 160° C. for 5 minutes using 40,000 pounds (about 14,900 Kg) of force applied to a 4-inch ram. The sample received a 2 minute preheat before being pressed.

The molded samples were cut into 2⅞×2⅞×0.50 inch sections. Testing was performed using the flaming mode of the NBS Smoke Chamber Test (ASTM E662-79) described heretofore. Test results are given in Table I.

TABLE I

| Example | Tripentylammonium Decamolybdate Parts By Weight | Dm/g* | Smoke Reduction % |
|---|---|---|---|
| 3 (control) | 0 | 68.40 | — |
| 4 | 2.0 | 36.26 | 47 |
| 5 | 5.0 | 35.89 | 48 |

*Dm/g = Maximum smoke density per gram of sample.

The improved smoke retardant vinyl chloride and vinylidene chloride polymer compositions obtained by the addition of tripentylammonium decamolybdate to the compositions are useful wherever smoke resistance is desirable, such as in carpets, house siding, plastic components for airplane and passenger car interiors, and the like.

I claim:

1. Tripentylammonium decamolybdate having the empirical formula $[H.(C_5H_{11})_3N]_4Mo_{10}O_{32}$ $n(H_2O)$ where "n" is an integer of from 0 to 4, characterized by major x-ray diffraction peaks at "d" spacings of 12.1Å, 11.6Å, 8.62Å and 8.34Å.

2. A smoke retarded composition comprising a vinyl chloride or vinylidene chloride polymer together with a smoke retardant amount of tripentylammonium decamolybdate having the empirical formula $$[H.(C_5H_{11})_3N]_4Mo_{10}O_{32}.nH_2O$$

where "n" is an integer of from 0 to 4, characterized by major x-ray diffraction peaks at "d" spacings of 12.1Å, 11.6Å, 8.62Å, and 8.34Å.

3. The smoke retarded composition of claim 2 wherein said amine molybdate has an average particle size from about 0.1 to about 100 microns.

4. The composition of claim 2 wherein said amine molybdate is present in an amount from 0.01 to about 20 parts by weight per 100 parts by weight of said polymer.